United States Patent
Cocking et al.

(10) Patent No.: US 6,529,841 B2
(45) Date of Patent: *Mar. 4, 2003

(54) APPARATUS AND METHOD FOR CONDUCTIVITY MEASUREMENT INCLUDING PROBE CONTAMINATION COMPENSATION

(75) Inventors: Andrew J. Cocking, Santa Cruz, CA (US); Wai Yin Cedric Chan, Santa Cruz, CA (US); James W. Livingston, Santa Cruz, CA (US)

(73) Assignee: Johnson Diversey, Inc., Sturtevant, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/841,783

(22) Filed: Apr. 24, 2001

(65) Prior Publication Data

US 2001/0029435 A1 Oct. 11, 2001

Related U.S. Application Data

(63) Continuation-in-part of application No. 09/078,400, filed on May 13, 1998, now Pat. No. 6,223,129.

(51) Int. Cl.$^7$ .............................................. G01N 27/48
(52) U.S. Cl. ........................ 702/65; 324/439; 137/359
(58) Field of Search ............................. 702/30, 32, 50, 702/65, 64; 73/335.05; 324/439, 444, 691; 137/392, 5; 422/82.02

(56) References Cited

U.S. PATENT DOCUMENTS

| | | | |
|---|---|---|---|
| 4,119,909 A | 10/1978 | DeBerry | 324/30 R |
| 4,756,321 A | 7/1988 | Livingston et al. | 134/56 D |
| 4,808,930 A | 2/1989 | Kaiser | 324/442 |
| 5,025,220 A | 6/1991 | Colvin et al. | 324/449 |
| 5,260,663 A | 11/1993 | Blades | 324/442 |
| 5,334,940 A | 8/1994 | Blades | 324/442 |
| 5,453,131 A | 9/1995 | Chan et al. | 134/18 |
| 5,500,050 A | 3/1996 | Chan et al. | 134/18 |
| 5,543,717 A | 8/1996 | Kordas | 324/444 |
| 5,581,189 A | 12/1996 | Brenn | 324/439 |
| 5,647,391 A | 7/1997 | Chan et al. | 137/93 |
| 5,973,503 A | 10/1999 | Kuipers et al. | 324/698 |
| 6,223,129 B1 * | 4/2001 | Chan et al. | 137/392 |
| 6,314,373 B1 * | 11/2001 | Prasser et al. | 324/691 |
| 6,392,416 B1 * | 5/2002 | Keech | 324/438 |

FOREIGN PATENT DOCUMENTS

EP  0 288 099 A1  10/1988

* cited by examiner

*Primary Examiner*—Patrick Assouad
(74) *Attorney, Agent, or Firm*—Gary S. Williams; Pennie & Edmonds LLP

(57) ABSTRACT

A conductivity measurement system provides one or more DC pulses to first and second electrodes submerged in an aqueous solution such as, for instance, the wash water of an industrial dishwasher. The voltage at the first electrode is measured at a sequence of at least three predetermined times after initiation of one of the DC pulse. A non-linear curve fitting function is applied to the sequence of at least three voltage measurements to calculate the voltage at the first electrode at the beginning of the DC pulse(s), commonly denoted as being at time $t=0$. The resulting calculated voltage at time $t=0$ is then used to calculate the conductivity of the solution, and/or to control operation of the a chemical dispenser, and/or to perform another predetermined system analysis or system control function. In addition, the difference between two of the measured voltages, such as the first and second measured voltages, is compared to a predetermined threshold value to determine whether the electrodes are so contaminated that polarization compensation is no longer feasible, thereby signaling that the electrodes should be cleaned or replaced.

51 Claims, 6 Drawing Sheets

APPARATUS AND METHOD FOR CONDUCTIVITY MEASUREMENT INCLUDING PROBE CONTAMINATION COMPENSATION

This application is a continuation-in-part of U.S. patent application Ser. No. 09/078,400, filed May 13, 1998, now U.S. Pat. No. 6,223,129.

The present invention relates generally to conductivity measurement systems and the low-cost probes thereof, such as used in commercial dishwashers, and particularly to conductivity measurement systems which compensate for probe contamination.

BACKGROUND OF THE INVENTION

Industrial dishwashers use conductivity measurement systems to maintain proper detergent concentrations in the dishwashers' wash water. Conductivity measurement systems are well known and typically include a probe that has first and second electrodes submerged in the wash water. A signal from a source circuit is applied to the electrodes to induce a current between the electrodes. This current, which is mirrored in the source circuit, is determined by dividing the voltage in the source circuit by the impedance of the source circuit. The conductivity of the wash water is then determined by dividing the current between the electrodes by the voltage across the electrodes.

Current flow in an aqueous solution, e.g., the wash water, is facilitated by the flow of ions between the electrodes. In an industrial dishwasher, the ions are provided by the detergent. Thus, increasing the detergent concentration results in a corresponding increase in the conductivity of the wash water. The relationship between wash water conductivity and detergent concentration for a particular detergent is typically stored in a look-up table, thereby allowing detergent concentration to be easily derived from wash water conductivity.

As current is induced between electrodes in an aqueous solution, ions begin accumulating on one of the electrodes. The ions accumulating on the electrode surface each occupy a finite space such that after a time period, t, there is no more available surface area on the electrodes on which ions may accumulate. This phenomena, known in the art as polarization, reduces current flow between the electrodes and may result in erroneous conductivity measurements which, in turn, lead to erroneous detergent concentration measurements. Conductivity measurements made during the wash cycle are used to control the adding of detergent to the wash water. Typically, detergent is added until the conductivity of the water reaches a predetermined level associated with a desired detergent concentration. When the electrodes of the dishwasher become polarized, the detergent concentration of the wash water is perceived by the dishwasher's control circuitry to be too low, thereby leading to the addition of detergent to wash water that may, in reality, already be at or above the desired detergent concentration.

Further, when used as described above, the electrodes undesirably accumulate non-conductive particles thereon which, in turn, reduce the effective area of the electrodes. As a result, contamination of the electrodes speeds the above-described polarization of the electrodes and, therefore, diminishes the useful life of the electrodes.

In theory, the effect of polarization upon conductivity measurements can be eliminated, or at least partially compensated, by calculating conductivity the instant current is induced between the electrodes, since at time $t=0$ ions have not yet accumulated on the electrodes. Here, the voltage between the electrodes must be measured just as the source signal that induces current in the wash water is asserted. Unfortunately, such an approach is not feasible. First, there are significant characteristic variations between ion species during the first 1 to 2 microseconds of aqueous current flow. Since the ion species of the detergent is typically unknown, measurements taken within the first 1 to 2 microseconds are unreliable. Second, it is very difficult to fabricate a circuit which can produce a source pulse and then immediately capture an analog reading produced by the source pulse.

U.S. Pat. No. 4,756,321 discloses an industrial dishwashing system in which a continuous AC signal is applied to first and second electrodes submerged in wash water to induce a current between the electrodes. The resulting current is measured over time, and then used to calculate the conductivity of the wash water. Conductivity is then converted into a logarithmically scaled detergent concentration. Here, the continuous current flow between the electrodes results in a continually increasing polarization of the electrodes. As a result, the electrodes must be either cleaned or replaced at regular intervals. The servicing of the electrodes is not only expensive, but also reduces operating efficiency of the dishwasher. Further, this system's inability to measure or predict electrode contamination makes it even more difficult to optimize the useful life of the electrode.

Another approach involves driving the electrodes with a pulsed DC signal as described, for instance, in U.S. Pat. No. 4,119,909. In that system, the pulsed DC signal induces short pulses of current between the electrodes in the wash water. Use of short current pulses reduces polarization and, thus, increases the useful life of the electrodes, as compared to the averaging technique disclosed in U.S. Pat. No. 4,756,321. However, conductivity measurements provided by this approach are nevertheless influenced by polarization. Further, this system, like that disclosed in U.S. Pat. No. 4,119,909, is unable to measure or predict electrode contamination. It is therefore difficult to accurately determine when or at what rate the measured conductivity deviates from the actual conductivity and, as a result, the accuracy with which this approach maintains the detergent concentration at a target level is compromised. It is thus also difficult to maximize the intervals at which the electrodes are cleaned or replaced and, therefore, difficult to maximize the useful life of the electrodes.

SUMMARY OF THE INVENTION

A conductivity measurement system provides one or more DC pulses to first and second electrodes submerged in an aqueous solution such as, for instance, the wash water of an industrial dishwasher. The voltage at the first electrode is measured at a sequence of at least predetermined times after initiation of one of the DC pulse. A curve fitting function is applied to the sequence of voltage measurements to calculate the voltage at the first electrode at the beginning of the DC pulse(s), commonly denoted as being at time $t=0$. The resulting calculated voltage at time $t=0$ is then used to calculate the conductivity of the solution, and/or to control operation of the a chemical dispenser, and/or to perform another predetermined system analysis or system control function. In addition, the difference between two of the measured voltages, such as the first and second measured voltages, is compared to a predetermined threshold value to determine whether the electrodes are so contaminated that polarization compensation is no longer feasible, thereby signaling that the electrodes should be cleaned or replaced.

Like components in the Figures are similarly labeled.

DETAILED DESCRIPTION OF THE PREFERRED EMBODIMENTS

Principles of the present invention are described below with reference to the industrial dishwasher 20 disclosed in U.S. Pat. No. 4,756,321, incorporated herein by reference, for simplicity only. It is to be understood that embodiments of the present invention may be used in other industrial dishwashers, or for any application in which it is desired to measure the conductivity of an aqueous solution. Accordingly, the present invention is not to be construed as limited to specific examples herein.

Figure 1:
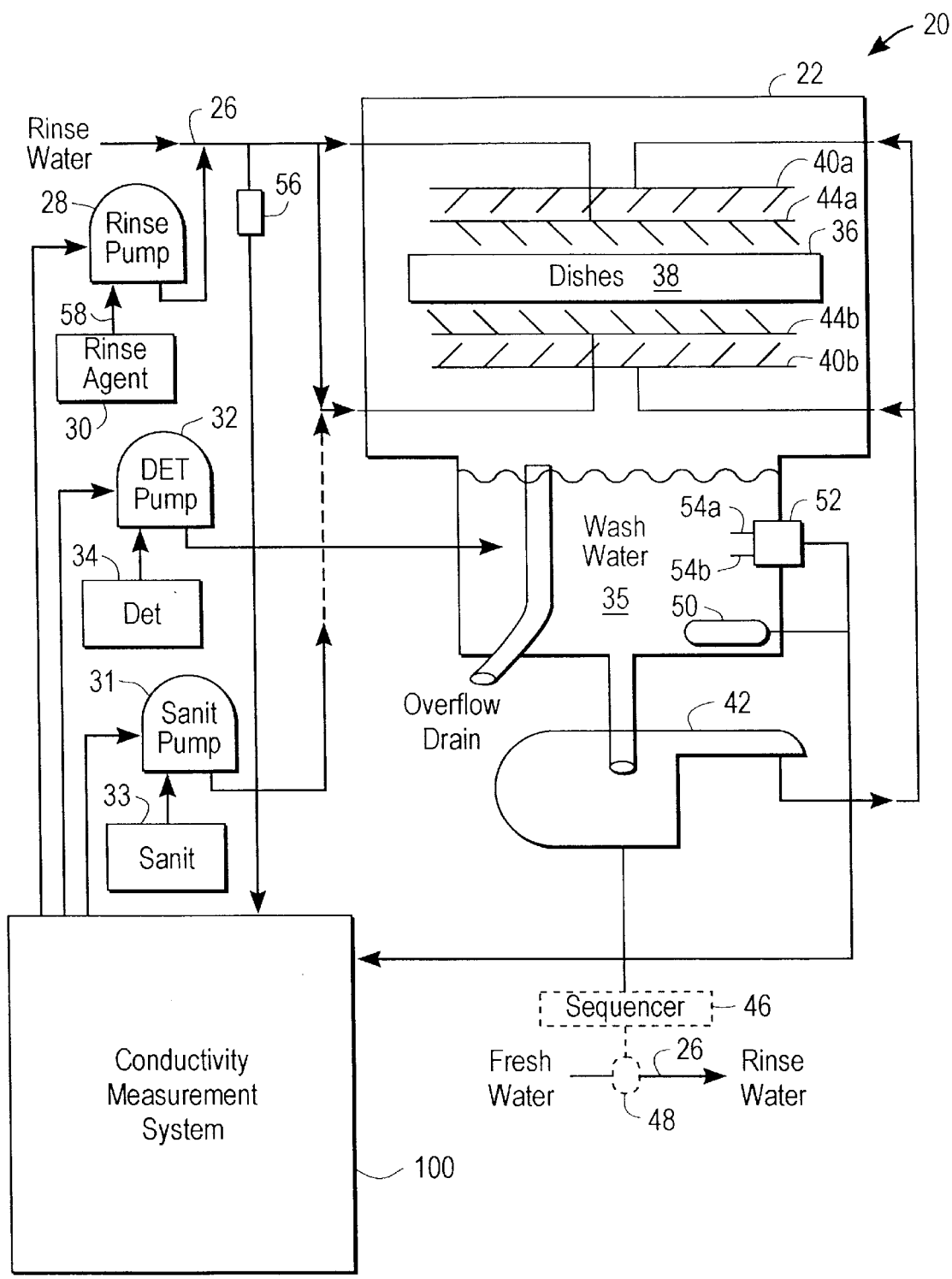
FIG. 1 is a block diagram of an industrial dishwasher in which a conductivity measurement system in accordance with the present invention is used.

Referring to FIG. 1, an industrial dishwasher 20 of the type described in U.S. Pat. No. 4,756,321 is shown to include a conductivity measurement system 100 in accordance with the present invention. System 100 is connected to a probe 52 having first 54a and second 54b electrodes submerged in a tank 35 of wash water used to wash dishes 38. In response to signals received from the probe 52, the system 100 provides control signals to a rinse pump 28, a detergent pump 32, and a sanitation pump 31 so as to ensure proper concentrations of a rinse agent, detergent, and a sanitation agent, respectively, within the wash water. The rinse agent is dispensed by pump 28 from a rinse agent supply 58, detergent is dispensed by pump 32 from a detergent supply 34, and sanitation agent is dispensed by pump 31 from a sanitation agent supply 33. For a discussion of the general operation of the dishwasher 20, as well as the advantages realized thereby, see U.S. Pat. No. 4,756,321.

Figure 2:
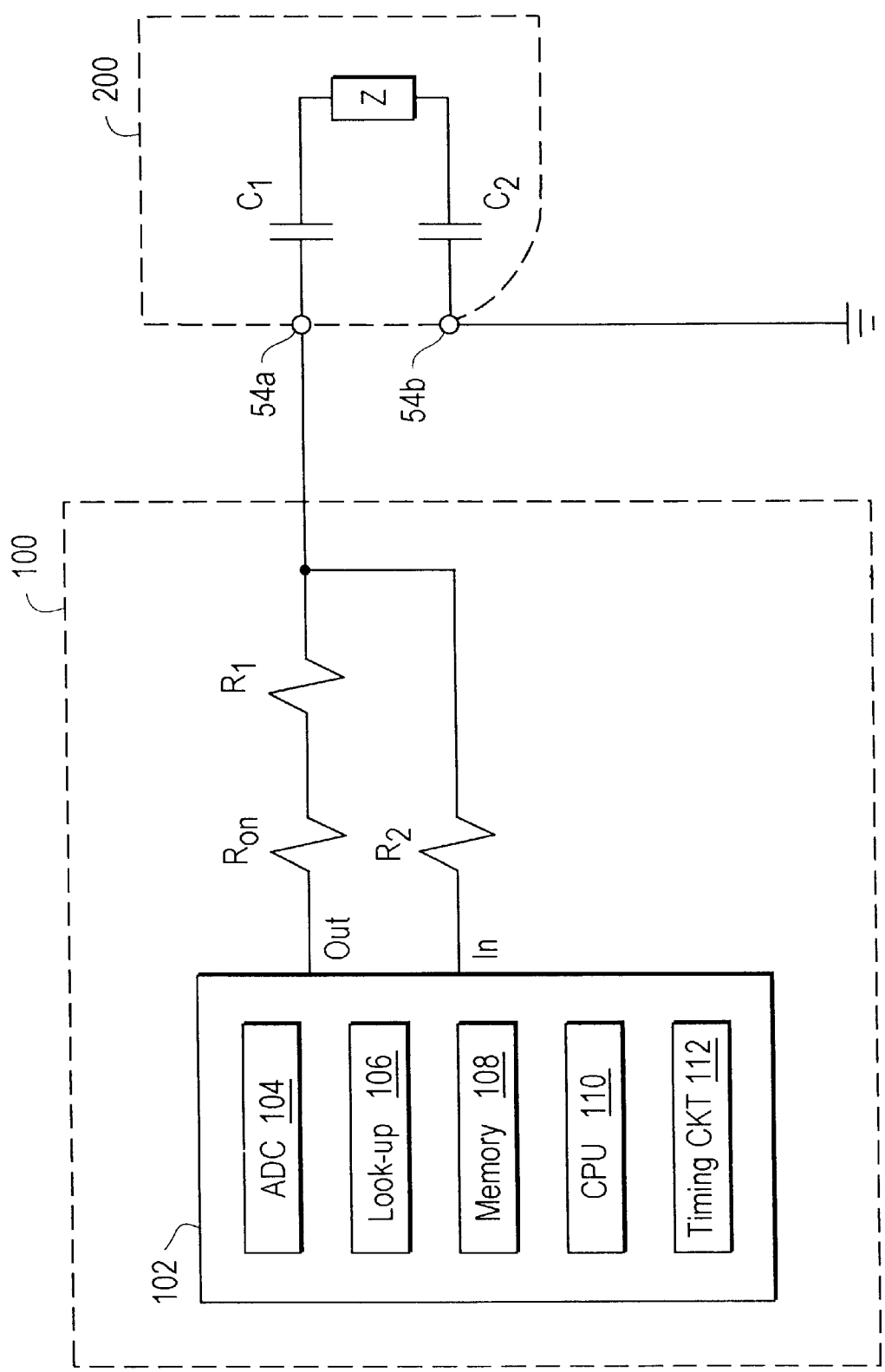
FIG. 2 is a block diagram of a micro-controller suitable for use in the conductivity measurement system of FIG. 1, including a schematic diagram of a four-layer capacitor modeling the polarization of wash water.

Referring to FIG. 2, the measurement circuit 100 includes a micro-controller 102 having an output terminal OUT coupled to the first electrode 54a via a resistor $R_1$, where resistor $R_{ON}$ models the on-resistance of the micro-controller 102. The resistor $R_1$ should be of a value suitable for the conductivity range of the wash water. In one embodiment, where $R_{ON}$ is 60 Ω, a value of 200 Ω is chosen for resistor $R_1$, as explained in detail below. The micro-controller 102 also has an input terminal IN coupled to the first electrode 54a of the probe via a resistor $R_2$ which serves as a series protection resistor for the ADC input terminal. Although the resistor $R_2$ should be as large as possible in order to provide maximum protection for the ADC input terminal, the resistor $R_2$ must also be small with respect to the input impedance of the ADC 104 in order to preserve signal strength. In one embodiment, where the micro-controller 102 is able to operate accurately with a source impedance as high as 10 kΩ, a value of 4.7 kΩ is selected for the resistor $R_2$. The second electrode 54b of the probe is tied to ground potential. Block 200 is an electrical representation on the wash water in the tank 35, where capacitors C1 and C2 form a four-layer capacitor which models polarization of the wash water, and the impedance element Z models the impedance of the wash water. Increases in electrode contamination are modeled by reducing the size of the capacitors.

The micro-controller 102 includes an analog-to-digital converter (ADC) 104, a look-up table 106, a memory 108 (for storing executable procedures, computed values, and other information), a central processing unit 110, and a timing circuit 112. The micro-controller 102 is connected to a voltage supply VDC and ground potential.

Figure 3:
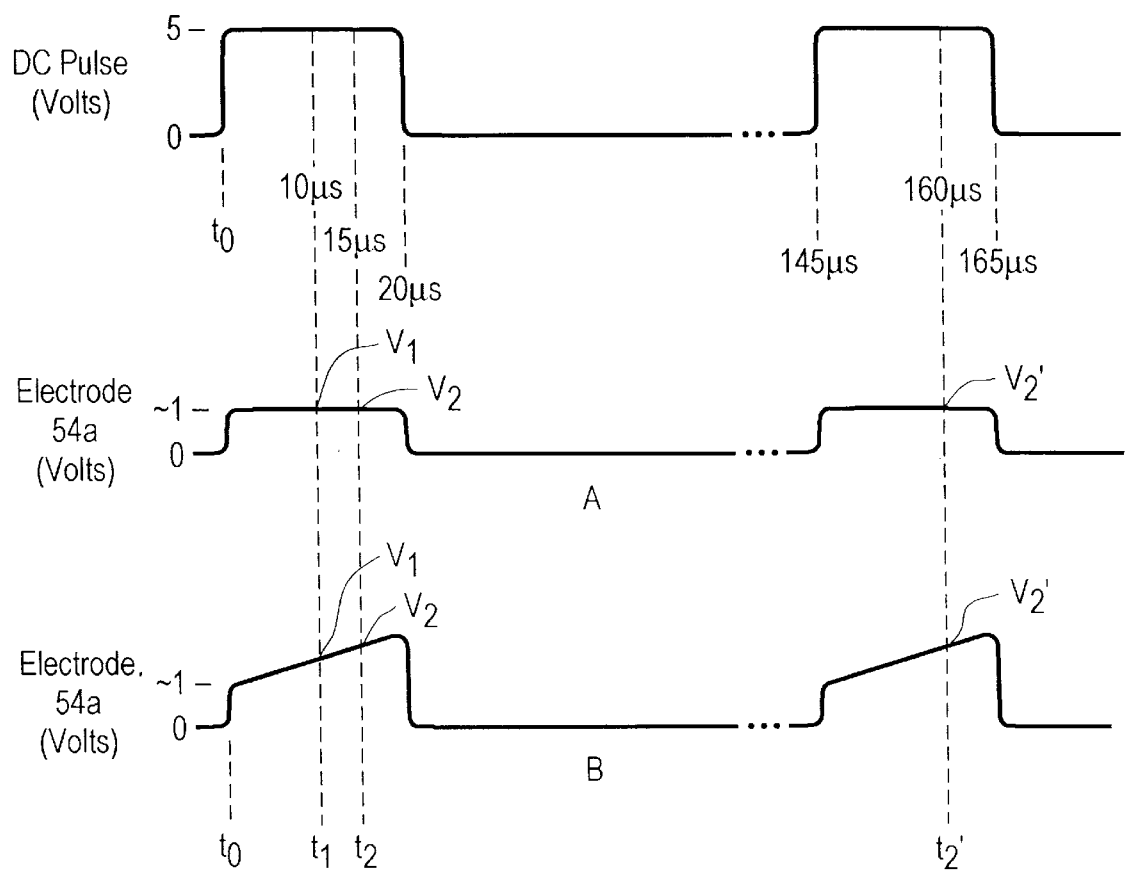
FIG. 3 is a timing diagram showing various signals associated with the operation of one embodiment of the present invention.

Referring to the timing diagram of FIG. 3, the micro-controller 102 generates at its output terminal OUT a DC pulse having a duration of T and an amplitude equal to $V_{DC}$. The voltage at the electrode 54a is measured at times $t_1$ and $t_2$, where $t_1 < t_2 < T$, thereby giving measured voltages $V_1$ and $V_2$, respectively, which are stored in the memory 108. If there is no polarization within the wash water, the measured voltages $V_1$ and $V_2$ will be equal, as illustrated by case A of FIG. 3. If, on the other hand, there is polarization, the current flow between the electrodes 54a and 54b will decrease between times $t_1$ and $t_2$ and, therefore, the voltage $V_2$ will be greater than the voltage $V_1$, as illustrated by case B in FIG. 3. The rate at which the voltage at the electrode 54a changes is assumed for the purposes of describing this embodiment to be substantially linear and, therefore, compensation techniques discussed below utilize linear algorithms. However, where greater accuracy is desired, more complex, non-linear compensation techniques are used. One embodiment of a conductivity measurement system using non-linear compensation techniques is described below with respect to FIGS. 5 and 6.

In calculating the conductivity of the wash water, linear regression is used to determine the voltage at electrode 54a at time t=0, i.e., at the beginning of the DC pulse. The voltage on the electrode 54a at time t=0 is given as:

$$V_0 = \frac{(V_1 t_2) - (V_2 t_1)}{(t_2 - t_1)}$$

Since the voltage $V_0$ corresponds to time t=0, the voltage $V_0$ is not influenced by the effects of polarization. Thus, the conductivity of the wash water, which is calculated using Ohm's law and the known K factor of the electrodes 54a and 54b, is not influenced by polarization within the wash water. In this manner, present embodiments compensate for polarization.

The difference between the first and second measured voltages, $V_{diff} = V_2 - V_1$, is indicative of the extent to which the electrodes are contaminated. Accordingly, if the difference value exceeds a predetermined threshold corresponding to the maximum degree of acceptable electrode contamination, the micro-controller 102 generates an alarm signal (e.g., a red light or other visual signal on the front panel of the device) alerting an operator of the system 20 that the electrodes 54a and 54b need to be cleaned or replaced. Further, in some embodiments, if the measured voltage $V_0$ at time t=0 is greater than a second predetermined threshold, the micro-controller 102 generates an alarm signal alerting the operator that the electrodes 54a and 54b are sufficiently contaminated so as to require servicing. In this manner, present embodiments facilitate servicing of the electrodes 54a and 54b before contamination becomes sufficient to degrade conductivity measurement accuracy.

In preferred embodiments, an inexpensive micro-controller such as, for instance, the 16C72, 16C73, or the 16C74, all available from Microchip Semiconductor Corp. is used for the micro-controller 102 in order to minimize cost. Since these micro-controllers are typically unable to take quick successive analog measurements, the first and second voltage measurements, $V_1$ and $V_2$, are sampled during two separate pulses, as explained below, where $V_{DC}$=5 volts, $R_{ON}$=60 Ω, $R_1$=200 Ω, $R_2$=4.7 kΩ, $t_1$=10 μs, $t_2$=15 μs, T=20 μs, and K=0.4.

Figure 4:
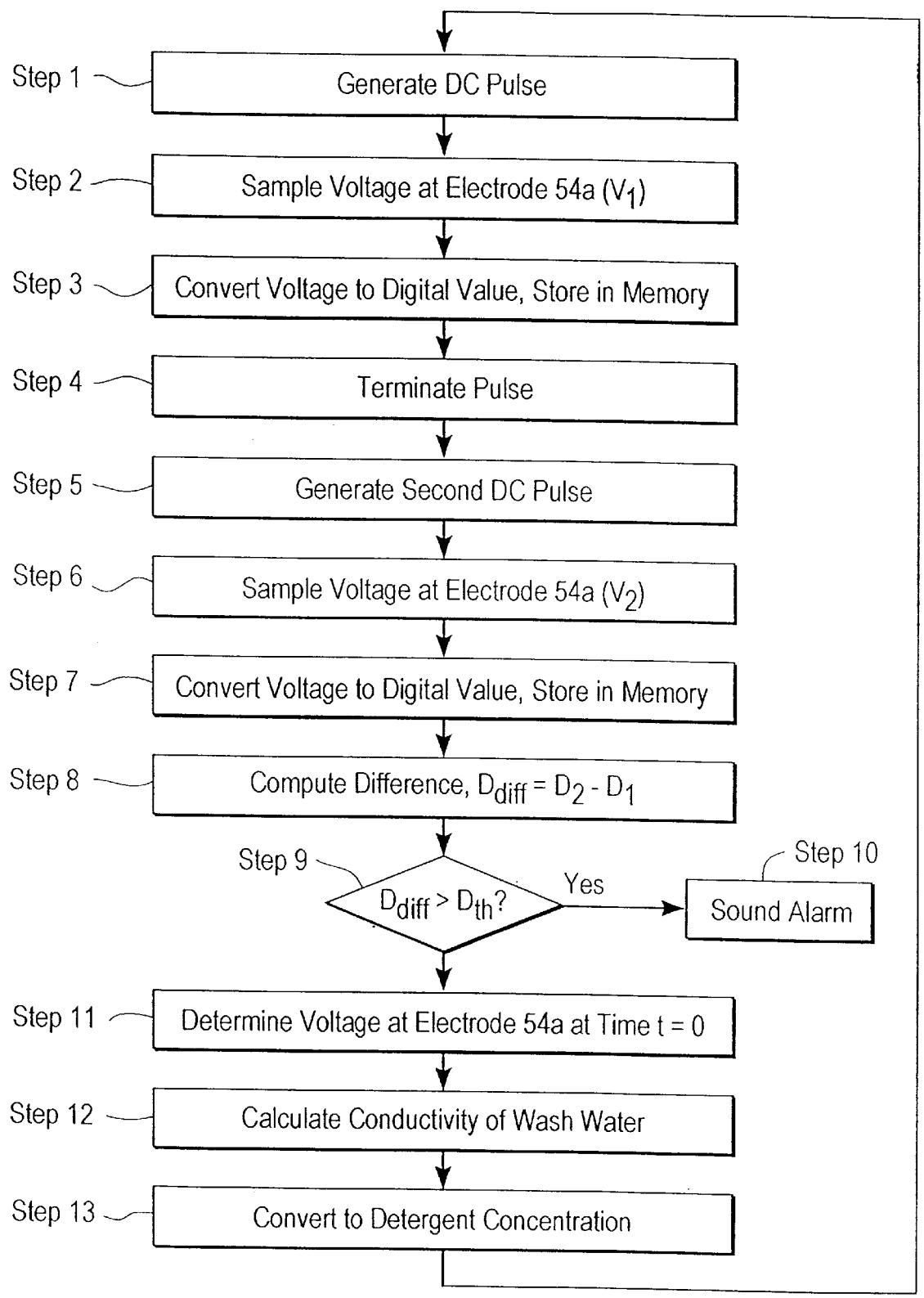
FIG. 4 is a flow chart illustrating operation of a conductivity measurement system in a preferred embodiment of the present invention.

Referring also to the flow chart of FIG. 4, the micro-controller 102 generates at time t=0 a first DC pulse having an amplitude of 5 volts (step 1). The DC pulse induces an electric field between the first and second electrodes 54a and 54b which, in turn, results in current flow between the electrodes 54a and 54b in the wash water. At time t=10 μs, the micro-controller 102 samples the voltage at the first electrode 54a via resistor $R_2$ (step 2). The resultant analog voltage $V_1$ is provided to the micro-controller 102 via its input terminal IN and is thereafter converted to a digital voltage $D_1$ via the ADC 104. The digital voltage $D_1$ is stored in the memory 108 (step 3). At time t=20 its, the micro-controller 102 terminates the first pulse, and the electrode 54a discharges to ground potential (step 4). After a predetermined period of time such as, for instance, 125 μs, the micro-controller 102 generates at its output terminal OUT a second DC pulse having an amplitude of 5 volts (step 5). The micro-controller 102 samples the voltage at the first electrode 54a at a time 15 μs after the second pulse is initiated (step 6). The resultant analog voltage $V_2'$ is converted to a digital voltage $D_2'$ via the ADC 104, and stored in the memory 108 (step 7).

As mentioned above, the conductivity measuring system 100 alerts an operator of the dishwasher 20 when electrode contamination exceeds acceptable levels. Here, the CPU 110 of the micro-controller 102 calculates the difference between the first and second stored digital (binary) voltages, $D_{diff}$=$D_1$-$D_2'$ (step 8), and then compares the difference voltage $D_{diff}$ to a predetermined threshold voltage $D_{th}$ (step 9). If the difference voltage $D_{diff}$ exceeds the predetermined threshold voltage $D_{th}$, the micro-controller 102 activates an alarm signal (e.g., a visual signal and/or an audible signal) to alert an operator of the dishwasher 20 that the electrodes need to be serviced (step 10).

The first and second voltages, $D_1$ and $D_2'$, are then processed by the CPU 110 according to the above-mentioned linear regression algorithm to determine the digital voltage $D_0$ on the first electrode 54a at the beginning of the first DC pulse, i.e., at time t=0 (step 11). In one embodiment, the digital voltages $D_1$ and $D_2'$ are stored as eight-bit numbers, where the binary number 255 corresponds to the analog value 5 (volts). The computed voltage at time t=0 and Ohm's Law are then used to calculate the conductance of the wash water (step 12). The conductance is converted to a detergent concentration using the look-up table 106 (step 13).

For example, where the digital voltages $D_1$ and $D_2'$ are equal to 65 and 70, respectively, the value $D_0$ (at time t=0) is equal to ((65)(15)−(70)(10))/(10+15)=55. The analog voltage $A_0$, which corresponds to the digital voltage $D_0$, is therefore equal to (5)(55)/(255)=1.08 volts. The current flowing in the circuit, i.e., through resistor $R_1$, is determined using Ohm's law (V=IR). Here, the current is equal to:

$$I=V/R=(5-1.08)/(60+200)=0.0151 \text{ amps.}$$

The uncorrected resistance of the element Z, and thus the resistance of the wash water, is equal to $$R=V/I=(1.08)/(0.0151)=71.5 \text{ Ω.}$$

The corrected resistance of the wash water is determined by dividing the uncorrected resistance by K, i.e., (71.5)/(0.4)= 178.75 Ω, which gives a conductance of 1/(178.75)=0.00559 mhos (or siemens)=5590 μsiemans. This measured conductance corresponds to the beginning of the DC pulse, i.e., time t=0, and is thus not influenced by polarization. In this manner, the conductivity measurement system 100 avoids the polarization-induced, erroneous detergent concentration measurements characteristic of conventional conductivity measurement systems.

The K factor is indicative of the electrodes' sensitivity and is typically between 0.1 and 10, where electrodes having a small K factor are more suitable for measuring low conductances and, conversely, electrodes having a large K factor are more suitable for measuring large conductances. A cell formed of an electrode pair "sees" a conductance divided by the K factor, e.g., a cell having a K factor equal to 0.1 sees a conductance that is ten times larger than the actual conductance of the wash water.

In some embodiments, the micro-controller 102 converts the calculated voltage $V_0$ into Beta units, a logarithmic unit of measure especially suited for use in determining the conductance of a detergent solution in an industrial dishwasher. Each unitary increase of the wash water conductivity level measured in Beta units corresponds to approximately a five (5) percent increase in the detergent concentration level (e.g., as measured in units of detergent per gallon of wash water). Beta units are well known in the art and are thus not discussed in detail herein. For a detailed discussion of Beta units, see U.S. Pat. No. 4,756,321.

In the above example, the cell formed by electrodes 54a and 54b has a K factor equal to 0.4. The Beta unit range when using such a cell is 0 to 60, which will yield a voltage change, as measured by the ADC 104 (FIG. 2), of between approximately 50 millivolts to 80 millivolts per Beta unit, depending on the actual conductivity. A Beta unit conversion routine executed by the micro-controller 102 uses a lookup table 106 (FIG. 2) to convert the voltage to Beta Units.

The typical conductivity of wash water without detergent is about 600 μmhos, and the typical conductivity of wash water with a maximum detergent concentration is about 12,000 μmhos. Thus, the above cell formed by electrodes 54a and 54b actually "sees" wash water conductivities ranging from 600/0.4=1500 μmhos 0.0015 mhos to 12,000/ 0.4=30,000 μmhos=0.03 mhos. This conductivity range corresponds to a resistivity range of 1/(0.03 mhos)=33.3 Ω to 1/(0.0015 mhos)=666.7 Ω. Thus, the maximum Beta count, i.e., 180, corresponds to the minimum wash water conductance, i.e., $R_{WATER}$=666.7 Ω. Using the voltage divider rule, $$\frac{180}{255} = \frac{666.7 \text{Ω}}{(R_{WATER} + R_{ON} + R1)}$$

where $R_{ON}$+$R_1$=277.8 Ω. Since as mentioned earlier $R_{ON}$= 60 Ω, a value of about 200 Ω is chosen for the resistor $R_1$. Applicants found that a value of 200 Ω for resistor $R_1$ limited the current to a safe level.

In a preferred embodiment, the above-described pulse sequence is repeated every 250 ms so as to provide four conductivity measurements per second, although the interval between pulse sequences may be adjusted as desired for particular applications.

Second Embodiment with Higher Measurement Speed and Higher Accuracy

Figure 5:
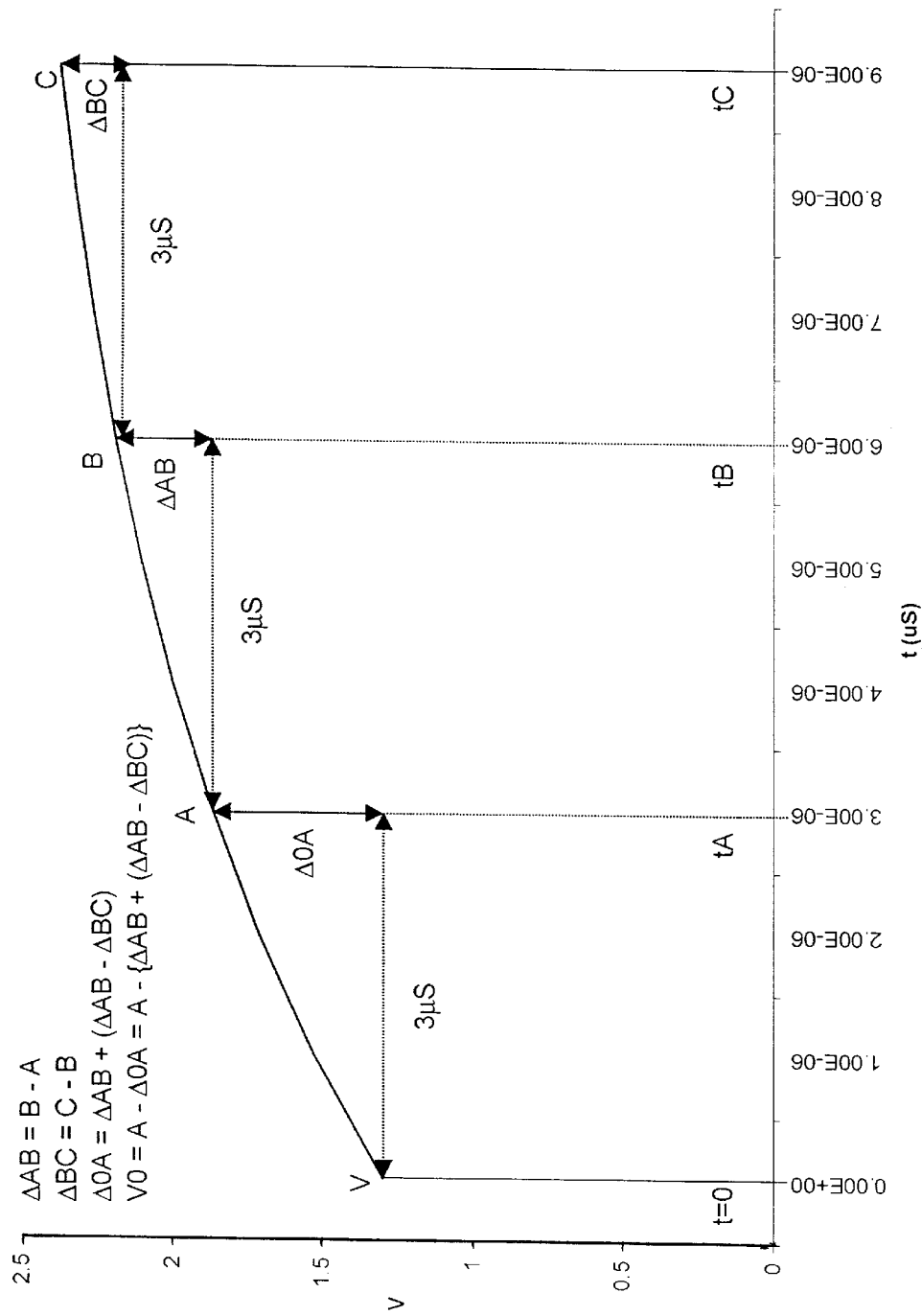
FIG. 5 is a graphical depiction of a curve fitting method of determining conductivity used in the second preferred embodiment.

Referring to FIG. 5, the voltage at the measurement input probe, induced by the DC voltage pulse on the OUT node of the processor, often exhibits a nonlinear trajectory over the measurement interval. The "measurement interval" is defined here to be the period of time from the beginning of the DC pulse to the last measurement of the voltage on the input probe. As shown in FIG. 5, the slope of the voltage at the input probe will tend to decrease during the measurement interval. As a result, the linear approximation used in the first embodiment will tend to produce a calculated $V_0$ voltage value that is higher than the true $V_0$ voltage. For instance, if the input probe voltage were measured at times tB and tC shown in FIG. 5, the calculated $V_0$ voltage value would be B−2ΔBC, and that value would be much higher than the actual $V_0$ voltage.

A second preferred embodiment of the present invention automatically compensates for the nonlinearity in the shape of input probe voltage characteristic as a function of time. As a result, the second preferred embodiment generates substantially more accurate conductivity values, especially when the probes are severely fouled. The probes are considered to be severely fouled when less then 10% of the probe surface is clean and available for use in determining the conductivity of an aqueous solution.

The apparatus of the second preferred embodiment of the present invention remains as shown in FIG. 2. However, the operation of the conductivity measurement system has been improved. In particular, the improved conductivity measurement system measures the input probe voltage at shorter intervals, closer to t=0, which improves the accuracy of the calculated $V_0$ voltage. In one implementation, the input probe voltage is measured at 3 μsec intervals, for instance at t=3 μsec, t=6 μsec, and t=9 μsec. In implementations in which the processor is unable to sample the input probe voltage at successive 3 μsec intervals, or if the analog to digital converter (ADC) in the processor is unable to convert analog inputs in successive 3 μsec intervals, the input probe voltage may be measured at these intervals, but with respect to different DC pulses. For instance, the input probe may be measured at t=3 μsec after a first DC pulse, at t=6 μsec after a second DC pulse, and at t=9 μsec after a third DC pulse. By using three input probe voltage measurements (or more) instead of two, the system is able to apply a nonlinear curve fitting function to the data so as to generate a more accurate estimate of the $V_0$ voltage.

The $V_0$ voltage is computed as follows. The input probe voltage is sampled at three intervals, producing voltage sample values A, B and C, as shown in FIG. 5. From these three values the following values are computed:

$$\Delta AB = B - A;$$

$$ABC = C - A;$$

Δ0A=ΔAB+(ΔAB−ΔBC); // this is a computed estimate of Δ0A $$V_0 = A - \Delta 0A = A - \{\Delta AB + (\Delta AB - \Delta BC)\}.$$

If the slope of the voltage signal is perfectly linear, the above computation produces the same result as the first embodiment. However, if the voltage signal is not linear, the second embodiment computes a Δ0A value that takes into account the change in slope of the voltage signal over the measurement interval.

The computational methodology shown above uses a linear approximation of a nonlinear curve fitting function. In other embodiments, especially embodiments in which greater computational power is available, the curve fitting function may be based on (A) more than three samples, and/or (B) may use a nonlinear curve fitting function instead of a linear approximation of a nonlinear curve fitting function. From another viewpoint, given a limited number of input probe voltage samples (but at least three such samples), the linear approximation of the nonlinear curve fitting function is functionally equivalent to the corresponding nonlinear curve fitting function, but more computationally efficient.

Once the voltage value $V_0$ has been determined, or at least approximated using a curve fitting methodology such as the one described above, the operation of the second embodiment is the same as the first. That is, the calculated voltage value $V_0$ is used to generate an output signal. For example, calculated voltage value $V_0$ may be used to the determine the conductivity of the wash water in the system, and/or to determine the concentration of detergent in the wash water. Based on either the conductivity value or detergent concentration value, the system then generates one or more control signals for controlling the operation of the device in which the conductivity measurement system is embedded. For instance, the control signals may be used to control the dispensing of detergent into the wash water of a dishwasher.

Figure 6:
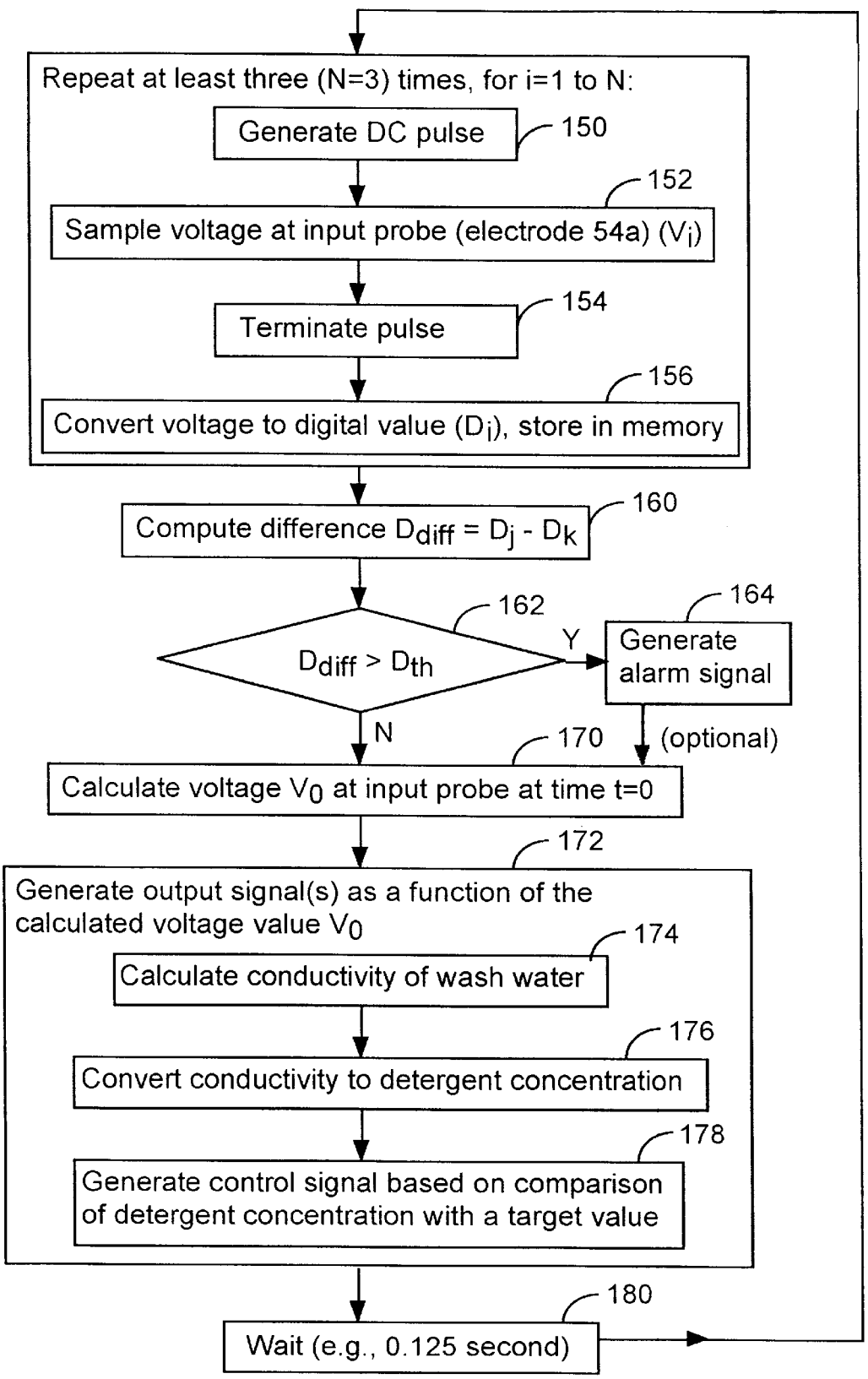
FIG. 6 is a flow chart illustrating operation of a conductivity measurement system in a second preferred embodiment of the present invention.

Referring to flow chart in FIG. 6, the conductivity measurement and device control procedure in an exemplary implementation of the second preferred embodiment is as follows. First, a sequence of at least three samples of the input probe voltage $V_i$ are taken and converted into digital values $D_i$ and stored in memory. In one implementation, this is done by repeating the steps of generating a DC pulse on the probe (150) and sampling the voltage at the input probe at an appropriate delay interval after the beginning of the pulse (152). The pulse is then terminated (154) and the sampled analog voltage is converted into a digital value $D_i$ (by the ADC internal to the micro-controller) and that value is stored in memory (156). The order of the pulse termination steps and analog to digital conversion steps 154 and 156 can be reversed. These steps 150, 152, 154 and 156 are repeated at least three times, each time using a different delay interval between activation of the DC pulse and the sample time, so as to develop a sequence of sample values representing the voltage at the input probe over a predefined measurement interval. For instance, the voltage at the input probe may be sampled at t=3 μsec after a first DC pulse, at t=6 μsec after a second DC pulse, and at t=9 μsec after a third DC pulse. In some embodiments, four, five or even more samples may be obtained so as to generate the data needed to more accurately compute the input probe voltage at time t=0.

Next, the difference between two of the voltage samples, or their digital values, is computed (160). The difference used here may be the difference between the second and first samples, but it also may be the difference between the third and second, or the third and first samples, depending on the implementation. The computed difference $D_{diff}$ is compared with a threshold value $D_{th}$ (162) and if the difference exceeds the threshold an alarm signal is generated (164).

If the alarm signal is not generated (or in some embodiments even if the alarm signal is generated), the procedure next computes a voltage $V_0$ representing a best approximation of the voltage at the input probe at time t=0 (170). The methodology for computing voltage $V_0$, or a digital equivalent thereof, using three sample voltage values and a linear approximation of a nonlinear curve fitting function, is described in detail above. As explained above, the computed voltage $V_0$ is a function of the conductivity of the aqueous solution in which the probe is immersed, and this value is computed in a way so as to compensate for fouling of the probe.

Next, the controller generates an output signal as a function of the calculated voltage $V_0$ (172). For instance, the voltage $V_0$ could be directly compared with a threshold value $V_{th}$ and a control signal could be turned on or off as a function of the result of the comparison. The threshold value $V_{th}$ in this example would be a value computed in advance to correspond to a target conductivity level of the aqueous solution, or equivalently would correspond to a target detergent concentration level, or a target concentration of other chemicals or constituents in the aqueous solution. Thus, at least in some embodiments, the calculated voltage $V_0$ for time t=0 does not need to be converted into a conductivity value or detergent concentration value, and instead can be used directly to control the operation of a device.

In one implementation of the second preferred embodiment, the calculated voltage $V_0$ for time t=0 is used to compute the conductivity of the wash water in a dishwasher (174), using the methodology described above with respect to the first preferred embodiment. The conductivity value is converted to a detergent concentration value (176), which again can be accomplished using the methodology described above with respect to the first preferred embodiment. Finally, a control signal is generated based on comparison of the detergent concentration value, or the conductivity value, or the voltage value, with a target value (178).

After the control value(s) are generated, in a preferred embodiment the control procedure waits for a predetermined period of time to elapse (180) before the procedure is repeated. For instance, the control procedure may wait until an eighth of a second has elapsed, or alternately is may wait until an eighth of second (or some other predetermined amount of time) has elapsed since the current iteration of the control procedure began, thereby ensuring that the entire control procedure is repeated a predefined number of times per second (or per minute, hour or other time period).

Alternate Embodiments

In the second embodiment, the number of input probe voltage measurements may be more than three, and the nonlinear curve fitting method used may differ from that described above. For instance, if four or more probe voltage measurements are taken, a higher order curve fitting function may be used.

In the preferred embodiments, the conductivity measurement system 100 is implemented as software running on a micro-controller. Appropriate program modules may be stored on a CDROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

What is claimed is:

1. A method of measuring representations of electrical conductivity of an aqueous solution which compensates for polarization, the method comprising:

generating a DC pulse to induce a current between first and second electrodes positioned within the solution;

sampling a voltage at the first electrode at a sequence of at least three predetermined time intervals after the generation of the DC pulse and generating a corresponding sequence of at least three voltage values in response thereto;

calculating, as a function of the at least three voltage values, a value corresponding to the voltage at the first electrode at a time contemporaneous with the generation of the DC pulse; and generating an output signal as a function of the calculated value, the output signal corresponding to the conductivity of the solution.

2. The method of claim 1, wherein generating the output signal includes:

determining a current flowing between the first and second electrodes and generating a current value in response thereto, the current value representing the current flowing in the solution;

generating the output signal as a function of the calculated value and the current value.

3. The method of claim 1, wherein the solution contains a detergent having a concentration, the method further comprising:

mapping, using a look-up table, the output signal to a concentration signal representing the concentration of the detergent in the solution.

4. The method of claim 1, further comprising:

subtracting a first one of the at least three voltage values from a second one of the at least three voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

5. The method of claim 1, further comprising:

subtracting one of the at least three voltage values from another one of the at least three voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

6. The method of claim 1, wherein the calculated value is calculated using a linear approximation of a nonlinear curve fitting function so as to compensate for nonlinearity, if any, in the sequence of at least three voltage values.

7. The method of claim 1, wherein the calculated value is calculated using a nonlinear curve fitting function so as to compensate for nonlinearity, if any, in the sequence of at least three voltage values.

8. A method of measuring representations of the electrical conductivity of an aqueous solution which compensates for polarization, the method comprising:

generating a plurality of DC pulses to induce a current between first and second electrodes positioned within the solution;

sampling a voltage at the first electrode at a first predetermined time interval after the generation of one of the plurality of DC pulses and generating a first voltage value in response thereto;

sampling the voltage at the first electrode at a second predetermined time interval after the generation of another one of the plurality of DC pulses and generating a second voltage value in response thereto, wherein the one and the another one of the DC pulses are not the same DC pulse;

sampling a voltage at the first electrode at a third predetermined time interval after the generation of one of the plurality of DC pulses and generating a third voltage value in response thereto;

calculating, as a function of at least the first, second and third voltage values, a value corresponding to the voltage at the first electrode at a time contemporaneous with the generation of one of the DC pulses; and generating an output signal as a function of the calculated value, the output signal corresponding to the conductivity of the solution.

9. The method of claim 8, wherein generating the conductivity signal includes:

determining a current flowing between the first and second electrodes and generating a current value in response thereto, the current value representing the current flowing in the solution;

generating the conductivity signal as a function of the calculated value and the current value.

10. The method of claim 8, wherein the solution contains a detergent having a concentration, the method further comprising:

mapping, using a look-up table, the output signal to a concentration signal representing the concentration of the detergent in the solution.

11. The method of claim 8, further comprising:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

12. The method of claim 8, further comprising:

subtracting one of the at least three voltage values from another one of the at least three voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

13. The method of claim 8, wherein the at least first, second and third voltage values comprise a sequence of voltage values, and the calculated value is calculated using a linear approximation of a nonlinear curve fitting function so as to compensate for nonlinearity, if any, in the sequence of values.

14. The method of claim 8, wherein the at least first, second and third voltage values comprise a sequence of voltage values, the calculated value is calculated using a nonlinear curve fitting function so as to compensate for nonlinearity, if any, in the sequence of values.

15. Apparatus for measuring electrical conductivity of an aqueous solution, comprising:

a probe having first and second electrodes, for submersion in a tank containing the solution;

a circuit for generating a DC pulse to induce a current between the first and second electrodes within the solution; and a controller programmed to:

sample voltage at the first electrode at a sequence of at least three predetermined time intervals after the generation of the DC pulse, and generate a corresponding sequence of at least three voltage values in response to the sampling of the voltage at the first electrode;

calculate, as a function of the at least three voltage values, a value corresponding to the voltage at the first electrode at a time contemporaneous with the generation of the DC pulse; and generate an output signal as a function of the calculated value, the output signal corresponding to the conductivity of the solution.

16. The apparatus of claim 15, wherein the controller includes software executed by the controller for determining a current flowing between the first and second electrodes and generating a current value in response thereto, the current value representing the current in the solution, and for generating the output signal as a function of the calculated value and the current value.

17. The apparatus of claim 15, wherein the solution contains a detergent having a concentration, and the controller includes software executed by the controller for mapping, using a look-up table, the output signal to a concentration signal representing the concentration of the detergent in the solution.

18. The apparatus of claim 15, wherein the controller includes software executed by the controller for:

subtracting a first one of the at least three voltage values from a second one of the at least three voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

19. The apparatus of claim 15, wherein the controller includes software executed by the controller for:

subtracting one of the at least three voltage values from another one of the at least three voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

20. The apparatus of claim 15, wherein the calculated value is calculated using a linear approximation of a nonlinear curve fitting function so as to compensate for nonlinearity, if any, in the sequence of at least three voltage values.

21. The apparatus of claim 15, wherein the calculated value is calculated using a nonlinear curve fitting function so as to compensate for nonlinearity, if any, in the sequence of at least three voltage values.

22. Apparatus for measuring electrical conductivity of an aqueous solution, comprising:

a probe having first and second electrodes, for submersion in a tank containing the solution;

a circuit for generating first and second DC pulses to induce a current between the first and second electrodes within the solution;

a controller programmed to:
sample a voltage at the first electrode at a first predetermined time interval after the generation of one of the plurality of DC pulses and generate a first voltage value in response thereto;
sample the voltage at the first electrode at a second predetermined time interval after the generation of another one of the plurality of DC pulses and generate a second voltage value in response thereto, wherein the one and the another one of the DC pulses are not the same DC pulse;
sample a voltage at the first electrode at a third predetermined time interval after the generation of one of the plurality of DC pulses and generate a third voltage value in response thereto;
calculate, as a function of at least the first, second and third voltage values, a value corresponding to the voltage at the first electrode at a time contemporaneous with the generation of one of the DC pulses; and
generate an output signal as a function of the calculated value, the output signal corresponding to the conductivity of the solution.

23. The apparatus of claim 22, wherein the controller includes software executed by the controller for determining a current flowing between the first and second electrodes and generating a current value in response thereto, the current value representing the current in the solution, and for generating the output signal as a function of the calculated value and the current value.

24. The apparatus of claim 22, wherein the solution contains a detergent having a concentration, and the controller includes software executed by the controller for mapping, using a look-up table, the output signal to a concentration signal representing the concentration of the detergent in the solution.

25. The apparatus of claim 22, wherein the controller includes software executed by the controller for:
subtracting the first voltage value from the second voltage value to generate a difference voltage;
comparing the difference voltage to a predetermined threshold voltage; and
generating an alarm signal if the difference voltage exceeds the predetermined threshold voltage, the alarm signal indicating that the electrodes are contaminated.

26. The apparatus of claim 22, wherein the controller includes software executed by the controller for:
subtracting one of the at least three voltage values from another one of the at least three voltage values to generate a difference voltage;
comparing the difference voltage to a predetermined threshold voltage; and
generating an alarm signal if the difference voltage exceeds the predetermined threshold voltage, the alarm signal indicating that the electrodes are contaminated.

27. The apparatus of claim 22, wherein the at least first, second and third voltage values comprise a sequence of voltage values, and the calculated value is calculated using a linear approximation of a nonlinear curve fitting function so as to compensate for nonlinearity, if any, in the sequence of at least three voltage values.

28. The apparatus of claim 22, wherein the at least first, second and third voltage values comprise a sequence of voltage values, and the calculated value is calculated using a nonlinear curve fitting function so as to compensate for nonlinearity, if any, in the sequence of at least three voltage values.

29. Apparatus for measuring electrical conductivity of an aqueous solution, comprising:
a probe having first and second electrodes, for submersion in a tank containing the solution;
a circuit for generating one or more DC pulses to induce a current between the first and second electrodes within the solution;
means for sampling voltage at the first electrode at first, second and third predetermined time intervals after the generation of respective DC pulses of the one or more DC pulses;
means for generating first, second and third voltage values in response to the sampling of the voltage at the first electrode at the first, second and third predetermined time intervals, respectively, calculating, as a function of at least the first, second and third voltage values, a value corresponding to the voltage at the first electrode at a time contemporaneous with the generation of any one of the one or more DC pulses; and generating an output signal as a function of the calculated value, the output signal corresponding to the conductivity of the solution.

30. The apparatus of claim 29, wherein the generating means includes means for determining a current flowing between the first and second electrodes and generating a current value in response thereto, the current value representing the current in the solution, and for generating the output signal as a function of the calculated value and the current value.

31. The apparatus of claim 29, wherein the solution contains a detergent having a concentration, and the generating means includes means for mapping, using a look-up table, the output signal to a concentration signal representing the concentration of the detergent in the solution.

32. The apparatus of claim 29, wherein the means for generating includes means for:
subtracting the first voltage value from the second voltage value to generate a difference voltage;
comparing the difference voltage to a predetermined threshold voltage; and
generating an alarm signal if the difference voltage exceeds the predetermined threshold voltage, the alarm signal indicating that the electrodes are contaminated.

33. The apparatus of claim 29, wherein the means for generating includes means for:
subtracting one of the first, second and third voltage values from another one of the first, second and third voltage values to generate a difference voltage;
comparing the difference voltage to a predetermined threshold voltage; and
generating an alarm signal if the difference voltage exceeds the predetermined threshold voltage, the alarm signal indicating that the electrodes are contaminated.

34. The apparatus of claim 29, wherein the at least first, second and third voltage values comprise a sequence of voltage values, and the calculated value is calculated using a linear approximation of a nonlinear curve fitting function so as to compensate for nonlinearity, if any, in the sequence of at least three voltage values.

35. The apparatus of claim 29, wherein the at least first, second and third voltage values comprise a sequence of voltage values, and the calculated value is calculated using a nonlinear curve fitting function so as to compensate for nonlinearity, if any, in the sequence of at least three voltage values.

36. A method of measuring representations of electrical conductivity of an aqueous solution which compensates for polarization, the method comprising:

generating a DC pulse to induce a current between first and second electrodes positioned within the solution;

sampling a voltage at the first electrode at a sequence of at least two predetermined time intervals after the generation of the DC pulse and generating a corresponding sequence of at least two voltage values in response thereto;

calculating, as a function of the at least two voltage values, a value corresponding to the voltage at the first electrode at a time contemporaneous with the generation of the DC pulse; and generating an output signal as a function of the calculated value, the output signal corresponding to the conductivity of the solution.

37. The method of claim 36, wherein generating the output signal includes:

determining a current flowing between the first and second electrodes and generating a current value in response thereto, the current value representing the current flowing in the solution;

generating the output signal as a function of the calculated value and the current value.

38. The method of claim 36, wherein the solution contains a detergent having a concentration, the method further comprising:

mapping, using a look-up table, the output signal to a concentration signal representing the concentration of the detergent in the solution.

39. The method of claim 36, further comprising:

subtracting a first one of the at least two voltage values from a second one of the at least two voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

40. A method of measuring representations of the electrical conductivity of an aqueous solution which compensates for polarization, the method comprising:

generating a plurality of DC pulses to induce a current between first and second electrodes positioned within the solution;

sampling a voltage at the first electrode at a first predetermined time interval after the generation of one of the plurality of DC pulses and generating a first voltage value in response thereto;

sampling the voltage at the first electrode at a second predetermined time interval after the generation of another one of the plurality of DC pulses and generating a second voltage value in response thereto, wherein the one and the another one of the DC pulses are not the same DC pulse;

calculating, as a function of at least the first and second voltage values, a value corresponding to the voltage at the first electrode at a time contemporaneous with the generation of one of the DC pulses; and generating an output signal as a function of the calculated value, the output signal corresponding to the conductivity of the solution.

41. The method of claim 40, wherein generating the conductivity signal includes:

determining a current flowing between the first and second electrodes and generating a current value in response thereto, the current value representing the current flowing in the solution;

generating the conductivity signal as a function of the calculated value and the current value.

42. The method of claim 40, wherein the solution contains a detergent having a concentration, the method further comprising:

mapping, using a look-up table, the output signal to a concentration signal representing the concentration of the detergent in the solution.

43. The method of claim 40, further comprising:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

44. Apparatus for measuring electrical conductivity of an aqueous solution, comprising:

a probe having first and second electrodes, for submersion in a tank containing the solution;

a circuit for generating a DC pulse to induce a current between the first and second electrodes within the solution; and a controller programmed to:

sample voltage at the first electrode at a sequence of at least two predetermined time intervals after the generation of the DC pulse, and generate a corresponding sequence of at least two voltage values in response to the sampling of the voltage at the first electrode;

calculate, as a function of the at least two voltage values, a value corresponding to the voltage at the first electrode at a time contemporaneous with the generation of the DC pulse; and generate an output signal as a function of the calculated value, the output signal corresponding to the conductivity of the solution.

45. The apparatus of claim 44, wherein the controller includes software executed by the controller for determining a current flowing between the first and second electrodes and generating a current value in response thereto, the current value representing the current in the solution, and for generating the output signal as a function of the calculated value and the current value.

46. The apparatus of claim 44, wherein the solution contains a detergent having a concentration, and the controller includes software executed by the controller for mapping, using a look-up table, the output signal to a concentration signal representing the concentration of the detergent in the solution.

47. The apparatus of claim 44, wherein the controller includes software executed by the controller for:

subtracting a first one of the at least two voltage values from a second one of the at least two voltage values to generate a difference voltage;

comparing the difference voltage to a predetermined threshold voltage; and generating an alarm signal if the difference voltage exceeds the predetermined threshold voltage, the alarm signal indicating that the electrodes are contaminated.

48. Apparatus for measuring electrical conductivity of an aqueous solution, comprising:

a probe having first and second electrodes, for submersion in a tank containing the solution;

a circuit for generating first and second DC pulses to induce a current between the first and second electrodes within the solution;

a controller programmed to:

sample a voltage at the first electrode at a first predetermined time interval after the generation of one of the plurality of DC pulses and generate a first voltage value in response thereto;

sample the voltage at the first electrode at a second predetermined time interval after the generation of another one of the plurality of DC pulses and generate a second voltage value in response thereto, wherein the one and the another one of the DC pulses are not the same DC pulse;

calculate, as a function of at least the first and second voltage values, a value corresponding to the voltage at the first electrode at a time contemporaneous with the generation of one of the DC pulses; and generate an output signal as a function of the calculated value, the output signal corresponding to the conductivity of the solution.

49. The apparatus of claim 48, wherein the controller includes software executed by the controller for determining a current flowing between the first and second electrodes and generating a current value in response thereto, the current value representing the current in the solution, and for generating the output signal as a function of the calculated value and the current value.

50. The apparatus of claim 48, wherein the solution contains a detergent having a concentration, and the controller includes software executed by the controller for mapping, using a look-up table, the output signal to a concentration signal representing the concentration of the detergent in the solution.

51. The apparatus of claim 48, wherein the controller includes software executed by the controller for:

subtracting the first voltage value from the second voltage value to generate a difference voltage;

comparing the difference voltage to a predetermined threshold voltage; and generating an alarm signal if the difference voltage exceeds the predetermined threshold voltage, the alarm signal indicating that the electrodes are contaminated.

* * * * *